(12) United States Patent
Barberi et al.

(10) Patent No.: US 11,619,651 B2
(45) Date of Patent: Apr. 4, 2023

(54) DEFORMABLE IMAGING PHANTOM FOR 4D MOTION TRACKING

(71) Applicant: MODUS MEDICAL DEVICES INC., London (CA)

(72) Inventors: Enzo Antonio Barberi, London (CA); Joseph Kerr, Orono, ME (US); Madeline Grace Perrin, London (CA); Kalin Ignatov Penev, London (CA); Nicholas Hartman, Parkhill (CA)

(73) Assignee: MODUS MEDICAL DEVICES INC., London (CA)

( * ) Notice: Subject to any disclaimer, the term of this patent is extended or adjusted under 35 U.S.C. 154(b) by 307 days.

(21) Appl. No.: 16/906,494

(22) Filed: Jun. 19, 2020

(65) Prior Publication Data
US 2020/0400716 A1    Dec. 24, 2020

Related U.S. Application Data

(60) Provisional application No. 62/863,932, filed on Jun. 20, 2019.

(51) Int. Cl.
*G01R 33/58* (2006.01)
*G01R 1/04* (2006.01)

(52) U.S. Cl.
CPC ............... *G01R 1/04* (2013.01); *G01R 33/58* (2013.01)

(58) Field of Classification Search
CPC .... G01R 1/04; G01R 33/58; G01R 33/56509; A61B 8/587; A61B 6/583
See application file for complete search history.

(56) References Cited

U.S. PATENT DOCUMENTS

| 6,635,486 | B2 | 10/2003 | Madsen et al. |
| 7,667,191 | B2 | 2/2010 | Serban et al. |
| 8,535,061 | B2 | 9/2013 | Boutchko et al. |
| 2013/0218001 | A1* | 8/2013 | Uhlemann ........... A61B 5/0036 600/1 |
| 2016/0133159 | A1* | 5/2016 | Saloux ................... G01D 18/00 73/866.4 |

(Continued)

FOREIGN PATENT DOCUMENTS

| KR | 20100047910 A | * | 5/2010 |
| KR | 10-1741946 | | 5/2017 |

(Continued)

OTHER PUBLICATIONS

Chang, Jina et al. "Development of a deformable lung phantom for the evaluation of deformable registration." Journal of applied clinical medical physics vol. 11,1 3081. Jan. 28, 2010 (Year: 2010).*

*Primary Examiner* — Daniel R Miller

(57) ABSTRACT

A deformable phantom, according to the present invention, has a housing made of a MRI invisible material enclosing a sealed reservoir filled with a MRI signal producing material, a piston slidably mounted within a sleeve and extending into the sealed reservoir, wherein the sleeve is slidably mounted to the housing and extends into the sealed reservoir, and a deformable structure within the sealed reservoir. The piston and sleeve move opposite to one another to conserve a constant fluid volume within the sealed reservoir as the piston moves in and out of the sealed reservoir to cause motion and/or deformation of the deformable structure.

38 Claims, 7 Drawing Sheets

(56) References Cited

U.S. PATENT DOCUMENTS

2017/0018205 A1    1/2017    Santhanam et al.

FOREIGN PATENT DOCUMENTS

| WO | 2007064951 A3 | 6/2007 |
| WO | 2008151202 A9 | 12/2008 |
| WO | 2014022480 A1 | 2/2014 |
| WO | 2015161337 A1 | 10/2015 |

\* cited by examiner

DEFORMABLE IMAGING PHANTOM FOR 4D MOTION TRACKING

FIELD OF THE INVENTION

The present invention relates to a magnetic resonance imaging (MRI) quality assurance (QA) phantom apparatus and, in particular, to a deformable imaging phantom for 4-Dimensional (4D) motion tracking.

BACKGROUND

Magnetic resonance imaging (MRI) is a well-established diagnostic imaging modality which is the gold standard for many applications due to its superior soft tissue contrast. The wide variety of contrast mechanisms can reveal both subtle and dramatic anatomical, functional, and pathological details with higher sensitivity and specificity than other imaging modalities.

More recently, the advantages of MRI are being used in image guided applications, such as neurosurgical planning and radiation planning and therapy. For example, in image guided radiation therapy, the ability to visualize tumors and real-time radiation dose distributions is expected to result in higher targeted dose to tumor regions with a concomitant decrease in radiation exposure to healthy tissue, resulting in more effective treatments and higher survival rates in afflicted patients. In some cases, image guided radiation therapy is the only viable treatment option for certain types of cancer. An important challenge related to radiation therapy is compensating for physiological motion that can confound precise targeting of moving tumors. Motion can be induced due to breathing, cardiac motion, peristaltic movement of the gastrointestinal tract, and the displacement of organs associated with the passage of digestive gases. Current techniques based on computed tomography (CT) and cone beam computed tomography (CBCT) imaging have poor soft tissue visualization and fail to accurately compensate for motion and tumor position. Therefore, they are subject to both significant errors and increased risk of injury to healthy tissue, due to positioning margins that are larger than the tumor size. Techniques based on breath hold and gating are typically employed to estimate tumor position, resulting in longer treatment times and additional risk associated with tumor position uncertainty.

Physiological tumor movement stems in hierarchy from the host organ. A force is applied to the host organ via common modalities such as breathing, cardiac beats, digestion, gas movement etc. This force creates both motion and deformation of the organ. Motion is defined as the displacement of the isocenter of the object; whereas, deformation is the change in shape through the application of pressure. Organ motion is capable of causing a simple 1:1 motion of the tumor volume which is currently modelled by known rigid inserts. What is not well understood is the effect of organ deformation. Organ deformation causes both tumor motion and deformation.

The recent introduction of MR-guided Linac systems into the clinical radiation therapy setting has presented a paradigm shift in the treatment of cancer, with the provision of exquisite soft tissue contrast only available through MR imaging. The ability to clearly visualize tumors and organs at risk in real time, and while moving, can provide clinicians with the ability to reduce treatment margins, increase dose to the tumor, and decrease dose to healthy tissue. It is envisioned that current techniques will be expanded to include real time physiological motion tracking with MR imaging, providing the ability to change or adapt the radiation beam to move with and precisely target moving tumors. This will eliminate the need to gate the radiation beam or employ breath hold techniques to localize the tumor. The result will be more effective treatment of cancers associated with high mortality due to their proximity to other sensitive or moving organs, such as pancreatic, liver and lung cancer.

Current state-of-the-art techniques for motion management involve the use of rigid structure motion phantoms to develop gating and rigid body tracking techniques. The development and implementation of next generation 4D motion tracking techniques using MR guidance for radiation therapy will rely on the use of effective and realistic QA tools to simulate 4D deformable motion associated with real tumor motion.

Accordingly, there is a need for QA phantoms with the ability to simulate a deformable anatomical structure for use with the next-generation 4D motion imaging systems.

SUMMARY OF THE INVENTION

A deformable phantom, according to the present invention, has a housing made of a MRI invisible material enclosing a sealed reservoir filled with a MRI signal producing material. A piston slidably mounted within a sleeve and extending into the sealed reservoir, wherein the sleeve is slidably mounted to the housing and extends into the sealed reservoir. A deformable structure is located within the sealed reservoir.

In another embodiment, the deformable structure has a deformable target therein, having a different proton or electron density from the surrounding deformable structure.

In another embodiment, the housing has a cylindrical shape with a continuous sidewall and opposing first and second end caps. The first end cap has an annular shape, defining and aperture, and the piston and sleeve are slidably mounted concentrically within the first end cap.

In another embodiment, the piston is connected to a motion assembly to drive the motion of the piston relative to the housing. The motion assembly may be configured to provide one or both linear and rotational motion to the piston.

In another embodiment, the deformable phantom is configured for use as an insert in a second phantom, such as a human thorax phantom.

In another embodiment, a deformable phantom, according to the present invention, has a housing made of a MRI invisible material and enclosing a sealed reservoir filled with a MRI signal producing material, wherein the sealed reservoir has a first volume portion and a second variable volume portion in fluid communication therewith. A piston is slidably mounted to the housing and extends into the sealed reservoir. A deformable structure is located within the sealed reservoir. The second variable volume portion varies to accommodate displacement of the fluid MRI signal producing material caused by the movement of the piston.

BRIEF DESCRIPTION OF THE DRAWINGS

In order that the invention may be more clearly understood, a preferred embodiment thereof will now be described in detail by way of example, with reference to the accompanying drawings, in which.

DESCRIPTION OF THE INVENTION

The deformable imaging phantom, according to the present invention, simulates physiological motion and deformation profiles of an anatomical structure for use in 4D motion tracking with next-generation MR imaging systems. The deformable imaging phantom may be used on its own or as an insert in another phantom, such as a human thorax section phantom to simulate the movement and/or deformation of physiological structures in a living patient. Although the present invention is described with reference to a deformable imaging phantom, certain embodiments may be used as a deformable phantom for other applications, such as dosimetry.

Figure 1:
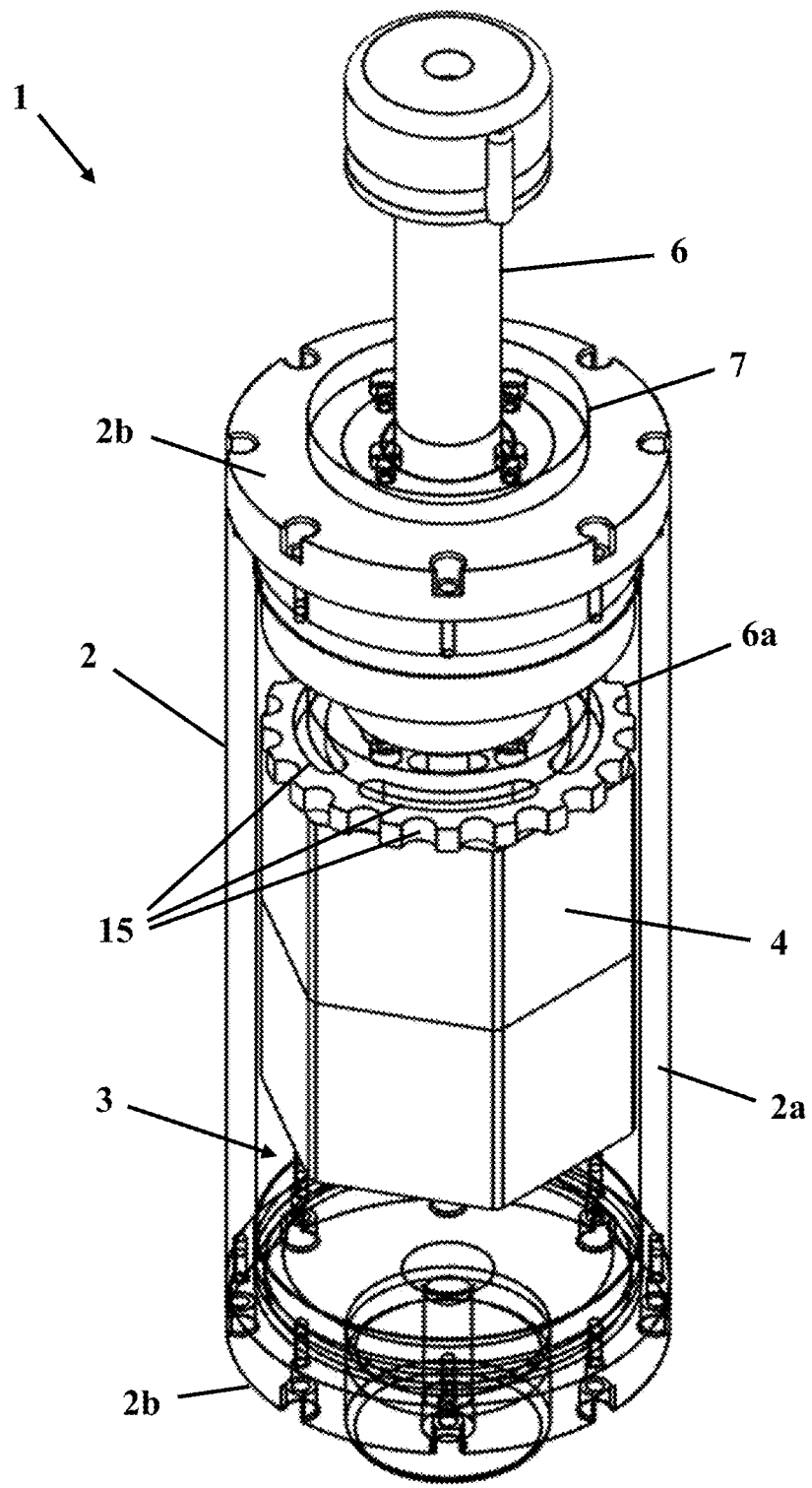
FIG. 1 is a perspective view of a deformable imaging phantom, according to the present invention.
Figure 2:
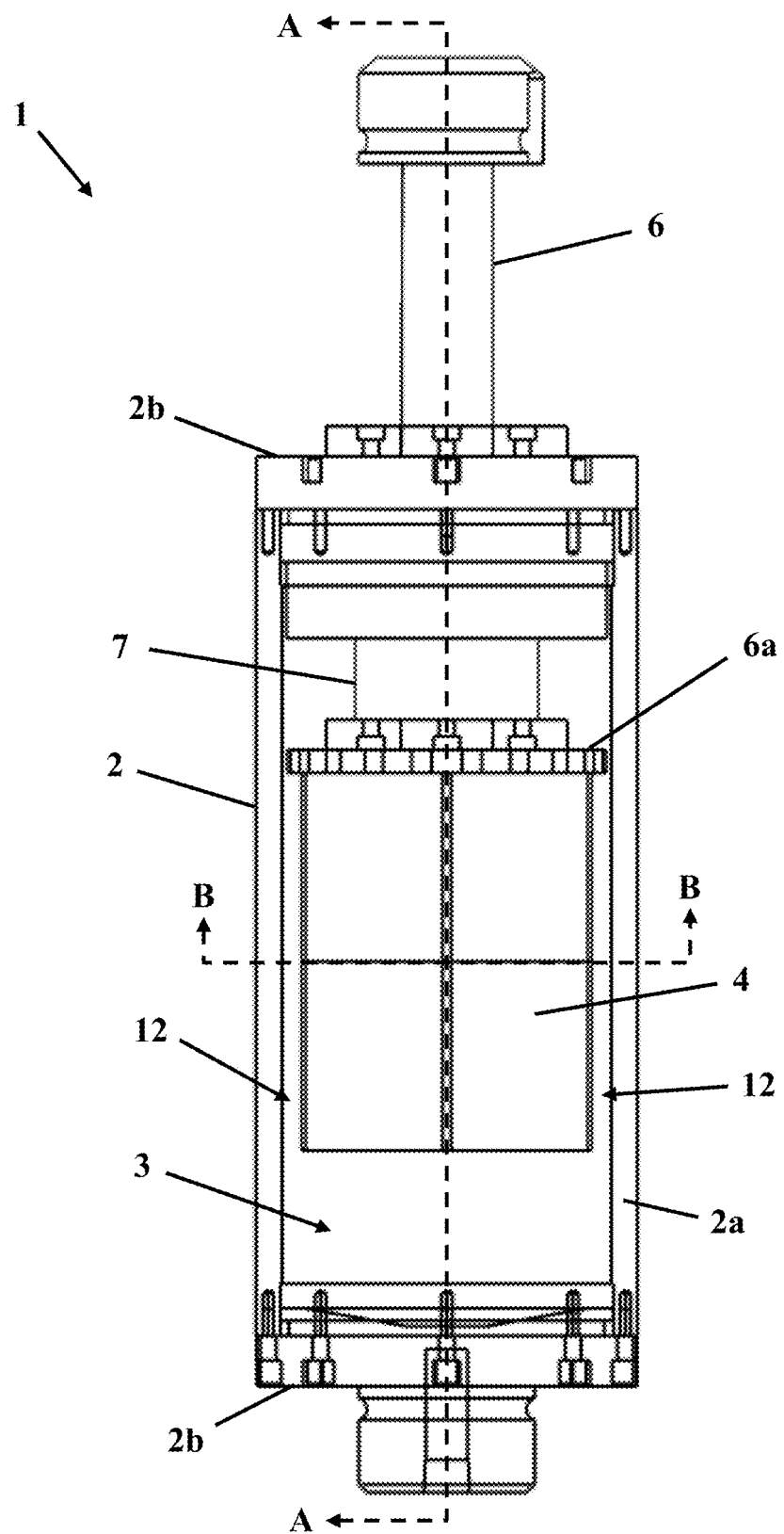
FIG. 2 is a side view of the deformable imaging phantom.

As shown in FIGS. 1 and 2, the phantom 1 has a housing 2 made of a rigid MRI invisible material, containing one or more sealed reservoirs 3 containing a fluid MRI signal producing material. Preferably, the housing 2 is made of acrylic, as it has closely matched susceptibility to human tissue, and the MRI signal producing material is an MRI contrast medium, such as aqueous solution with a close susceptibility match to human tissue. The aqueous solution is doped with one or more suitable T1 and T2 relaxivity modifiers, adjusted to give physiologically relevant T1 and T2 values with specific contrast between healthy tissue and tumors. Alternatively, the housing may be another human tissue equivalent susceptibility-matched plastic and the MRI contrast media may be an aqueous solution with added viscosity modifiers, mineral oil, silicone oil, vegetable oil, propylene glycol, or a gel that produces an MRI signal. Preferably, the relaxivity modifier is one or more of: copper (II) sulfate ($CuSO_4$), manganese (II) chloride ($MnCl_2$), gadolinium (III) chloride ($GdCl_3$), or other salts and chelates of paramagnetic metals that are soluble or freely dispersed in the MRI contrast media, superparamagnetic iron oxide nanoparticles (SPIONs), or micelles. Preferably, the phantom 1 is configured for multimodality applications, including two or more of: MRI, CT (MV or kV), and ultrasound. In addition to multimodality imaging applications, the phantom 1 may be configured for use in dosimetry, gel dosimetry, deformable dose accumulation, double inversion recovery (DIR), targeting, or gating applications.

Figure 3:
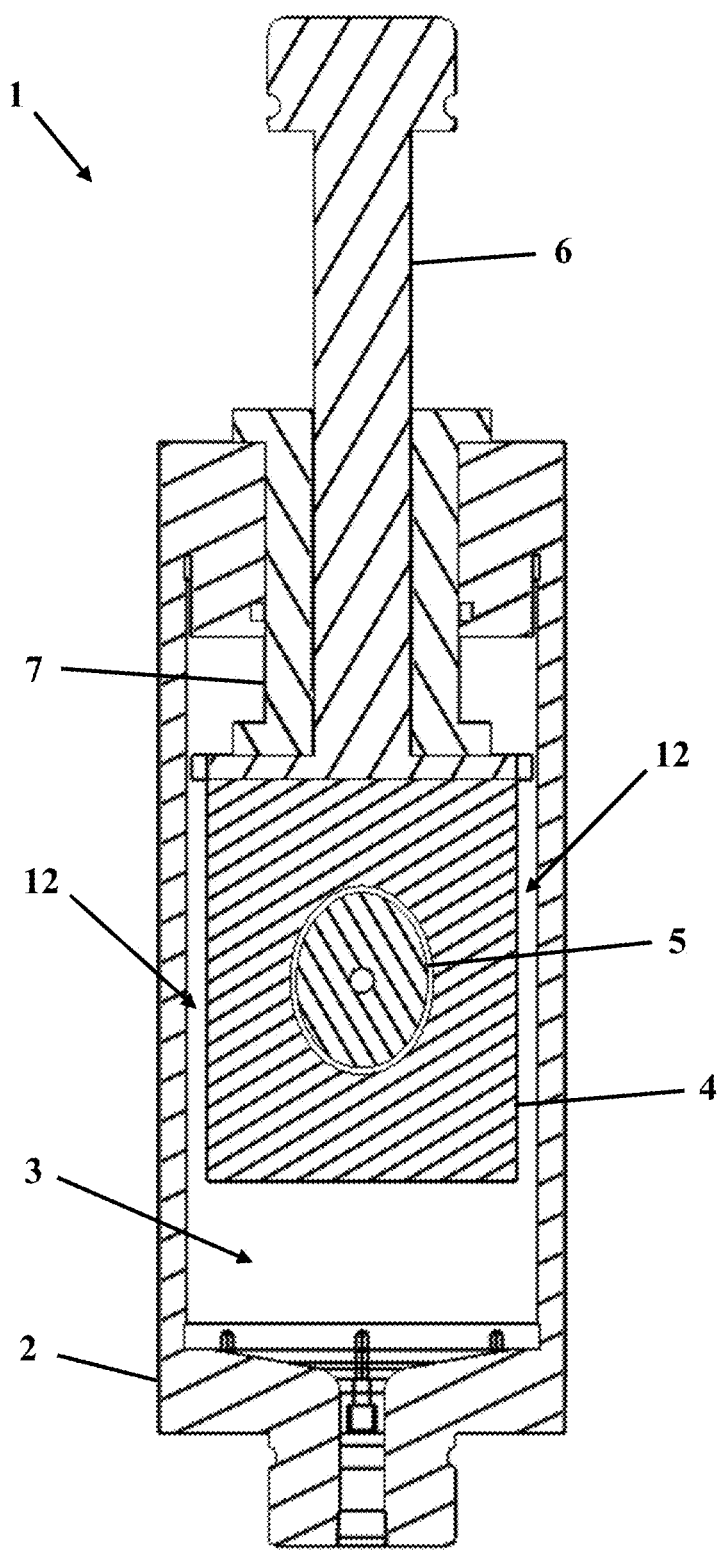
FIG. 3 is a side sectional view of the deformable imaging phantom, along the line A-A in FIG. 2.

As shown in FIG. 3, the housing 2 of the phantom 1 has a generally cylindrical shape, with a continuous side wall 2a and two opposing end caps 2b. The housing 2 defines a sealed reservoir 3 filled with an MRI contrast media and a deformable structure 4 with one or more organ or tumor shaped targets 5 within the deformable structure 4. The targets 5 are made of a MRI imageable soft, flexible material, such as silicone rubber. Preferably, the deformable structure 4 is made of an open cell polyurethane foam, but other similar materials may be used, such as open cell poly(vinyl alcohol) foam, open cell silicone foam, closed cell foams, other foams, or other viscoelastic materials. Alternatively, continuous materials with viscoelastic properties and intrinsic MRI signal, such as urethane rubbers, silicone rubbers, or thermoplastic elastomers (such as styrene-ethylene-butylene-styrene co-polymer) may be used on viscoelastic hydrogels, based on natural or artificial gel forming polymers, such as gelatin, agarose, poly(vinyl alcohol), acrylamide-based polymers, or combinations thereof, with or without cross-linking agents, such as metal ion salts, aldehydes, amines, or acrylamides. Preferably, the deformable structure 4 is in free contact with the MRI contrast media, which fills the sealed reservoir 3 and the interstitial spaces in the deformable structure 4, if any. Alternatively, the deformable structure 4 may be enclosed in a thin-walled barrier, or coating, of deformable material, such as natural or artificial rubber, silicone, fluorosilicone rubber, or similar inert elastomers. Where a foam material is used, it is preferably impregnated with MR contrast media using a vacuum for air bubble removal to minimize MR and CT imaging artifacts in the target zone.

Figure 6:
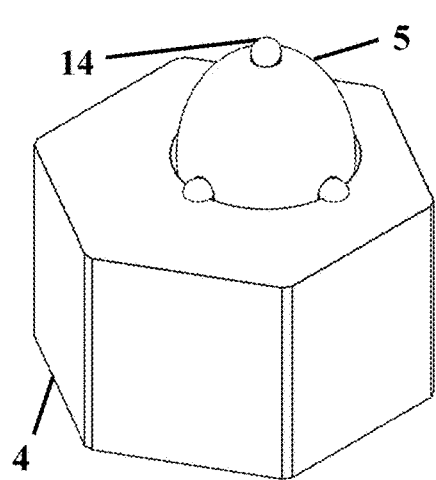
FIG. 6 is a perspective view of the deformable structure and target of the deformable imaging phantom.
Figure 7:
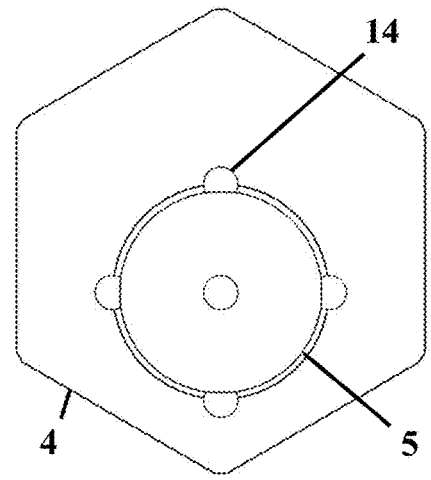
FIG. 7 is a top view of the deformable structure and target, shown in FIG. 6.
Figure 8:
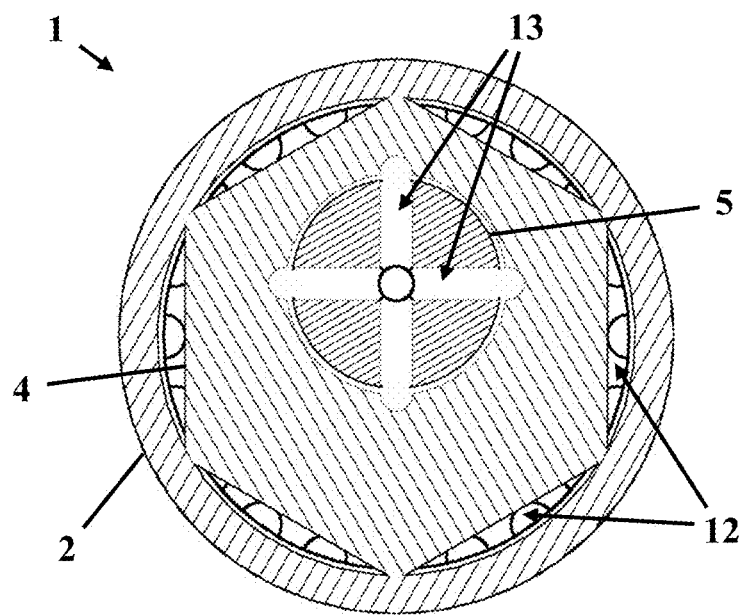
FIG. 8 is a bottom sectional view of the deformable imaging phantom, shown along the line B-B in FIG. 2.
Figure 9:
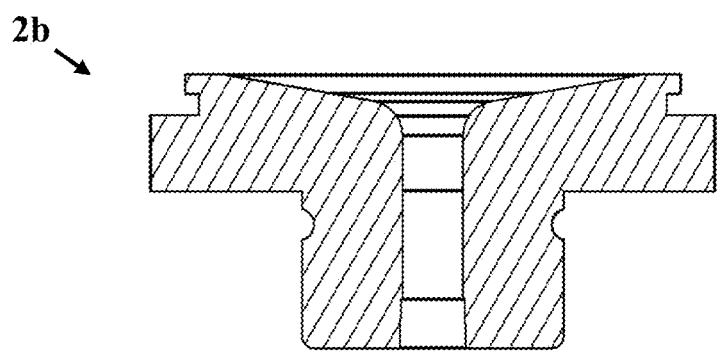
FIG. 9 is a detail sectional view of the end cap of the deformable imaging phantom, shown along the line A-A in FIG. 2.

As shown in FIGS. 6-8, the deformable structure 4 has a hexagonal cross-sectional shape to provide flow channels 12 between the deformable structure 4 and the sidewall 2a of the housing 2. These channels 12 facilitate fluid flow to reduce turbulent imaging artifacts and reduce resistance to motion. Other cross-sectional shapes may be used that provide channels 12 for adequate fluid flow. The deformable structure 4 is molded with one or more targets 5 with an offset from the axial centre of the deformable structure 4.

Where a foam material is used for the deformable structure 4, MR image contrast with the target 5 is provided by the difference in proton (hydrogen) density, which MR imaging is particularly well suited to differentiate. Where a continuous medium is used, it will show its own intrinsic MR signal. The deformable structure 4 and target 5 also exhibit a difference in electron density, to which x-ray Computed Tomography (CT) imaging is well suited. Therefore, multimodality 4D imaging is possible in certain embodiments. The hardness of the material of the target 5 should be such that it permits deformability and flexibility in operation. Preferably, the silicone rubber material of the target 5 has a Shore 00 scale hardness, more preferably, the target 5 has a hardness between Shore 00-10 and Shore 00-30.

Optionally, instead of one or more targets 5, the deformable structure 4 may include voids or regions having a different composition or density of material. The internal organ/tumor model may include varying density foam, rigid objects or tethers, with or without a coating or barrier (for alternative interior contrast). The material is not limited to foam and could be a urethane rubber, thermoplastic elastomer (such as styrene-ethylene-butylene-styrene co-polymer), latex balloon, or hydrogel, with or without the addition of high-density, non-metallic, non-conductive powder for increased CT contrast. The different proton or electron densities of these regions results in different imaging properties. In FIGS. 3 and 6-8, the deformable structure 4 is illustrated with a single off-centre ellipsoidal target 5, but the one or more targets 5 or variable density regions in the deformable structure 4 may have other positions and geometries, such as a spherical shape or the physiological shape of an organ or tumour.

Optionally, the target 5, the deformable structure 4 or both may be used as deformable dosimeters for measurement of the dose and distribution of the ionizing radiation delivered to the target 5 and/or the deformable structure 4, as registered by MRI, x-ray CT, optical methods or any other compatible imaging modality, either in situ or following disassembly of the device. Such deformable dosimeters can be formed by addition of radiation indicators, such as acrylamide and bis-acrylamide monomers, to a deformable hydrogel, where the radiation-induced polymerization can be determined by MRI, CT or optical methods. Other suitable indicators include radiochromic dyes, which may be added to a deformable hydrogel or to urethane or silicone rubber materials, where the radiation-induced color change can be determined by optical methods. Alternatively, the radiation-induced cross-linking of silicone or urethane rubbers, doped with appropriate additives, may be detected by MRI or CT imaging and used to measure the accumulated radiation dose. In the further alternative, an ion chamber or other radiation measurement device may be placed in a recess in the target 5, which may act as or receive an ion chamber holder.

As shown in FIGS. 3-5 and 10, one end cap 2b of the housing 2 contains a dual action mechanism made up of a piston 6 and a reciprocating sleeve 7, which are attached to the housing 2 and extend into the sealed reservoir 3. Preferably, the end cap 2b has an annular shape and the reciprocating sleeve 7 and piston 6 are slidably mounted concentrically within the end cap 2b. The end cap 2b, the reciprocating sleeve 7, and the piston 6 are sealed to prevent the MRI contrast media in the sealed reservoir 3 from leaking between any of the adjacent surfaces. Preferably, a seal 8 is mounted on the end cap 2b, between the end cap 2b and the reciprocating sleeve 7, and another seal 8 is mounted on the reciprocating sleeve 7, between the piston 6 and the reciprocating sleeve 7. Optionally, a secondary space may be provided between the reciprocating sleeve and piston for in-service use to repair leakages. Alternatively, another type or configuration of gasket or seal may be used to prevent MRI contrast media from leaking out of the sealed reservoir 3.

Figure 4:
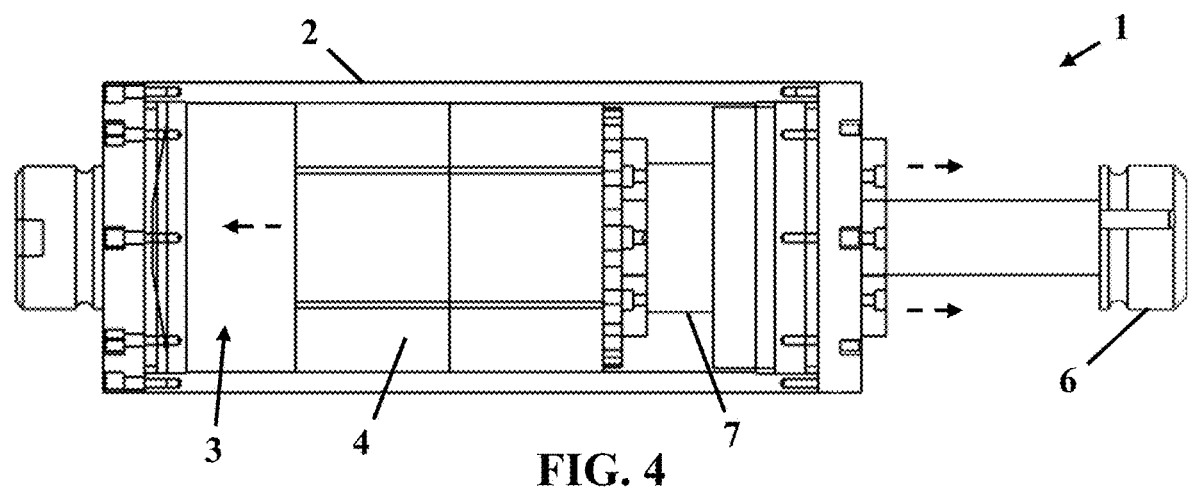
FIG. 4 is a side view of the deformable imaging phantom, shown with the piston in a fully retracted position.
Figure 5:
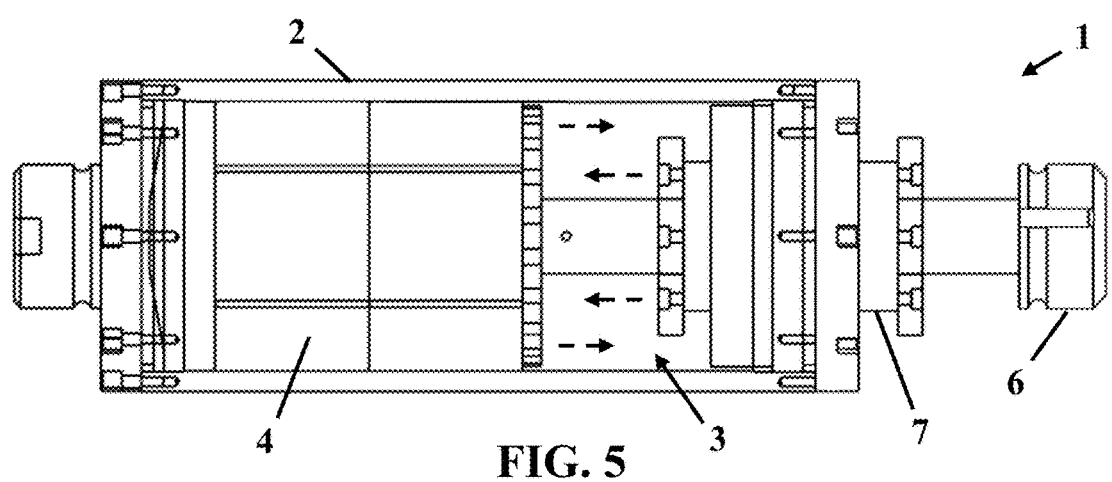
FIG. 5 is a side view of the deformable imaging phantom, shown with the piston in an extended position.
Figure 12:
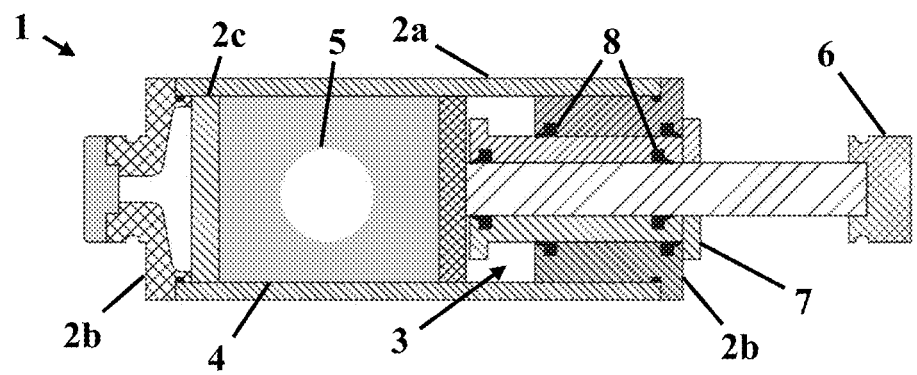
FIG. 12 is a side sectional view of another embodiment of the deformable imaging phantom.
Figure 13:
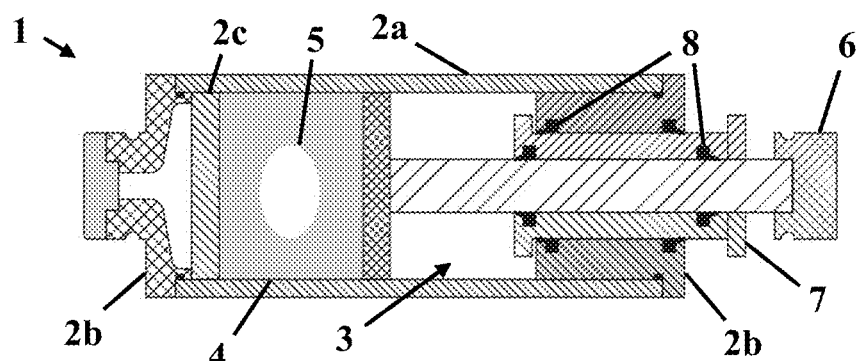
FIG. 13 is a side sectional view of the deformable imaging phantom shown in FIG. 12, with the piston in an extended position to illustrate deformation of the target.

The piston 6 and reciprocating sleeve 7 are configured to conserve a constant fluid volume within the sealed reservoir 3 as the piston 6 and reciprocating sleeve 7 move between a retracted position, shown in FIGS. 4 and 12, and an extended position, shown in FIGS. 5 and 13. Accordingly, as the piston 6 moves into the sealed reservoir 3, thereby displacing a volume of the MRI contrast media contained therein, the reciprocating sleeve 7 moves out of the sealed reservoir 3 to compensate. Conversely, when the piston 6 moves out of the sealed reservoir 3, the reciprocating sleeve 7 moves into the sealed reservoir 3.

Alternatively, rather than using a piston 6 and reciprocating sleeve 7 to conserve a constant fluid volume, the sealed reservoir 3 may be configured with a first volume portion and a second variable volume portion to accommodate the displacement of the fluid within the first volume portion of the sealed reservoir 3, caused by the movement of the piston 6 in and out of the sealed reservoir 3. Preferably, the sealed reservoir 3, according to this embodiment, is configured as described in U.S. Pat. No. 10,180,484 B2 or 10,310,048 B2 in the name of the present applicant. The first volume portion is the space defined by the sidewall 2a and the end caps 2b of the housing 2. The second volume portion is an expandable chamber or an expandable bladder attached to the housing 2 and in fluid communication with the first volume portion. Alternatively, the second variable volume portion may be provided by way of a compressible deformable structure 4 within the sealed reservoir 3, which compresses in response to the movement of the piston 6 into the sealed reservoir 3.

Figure 10:
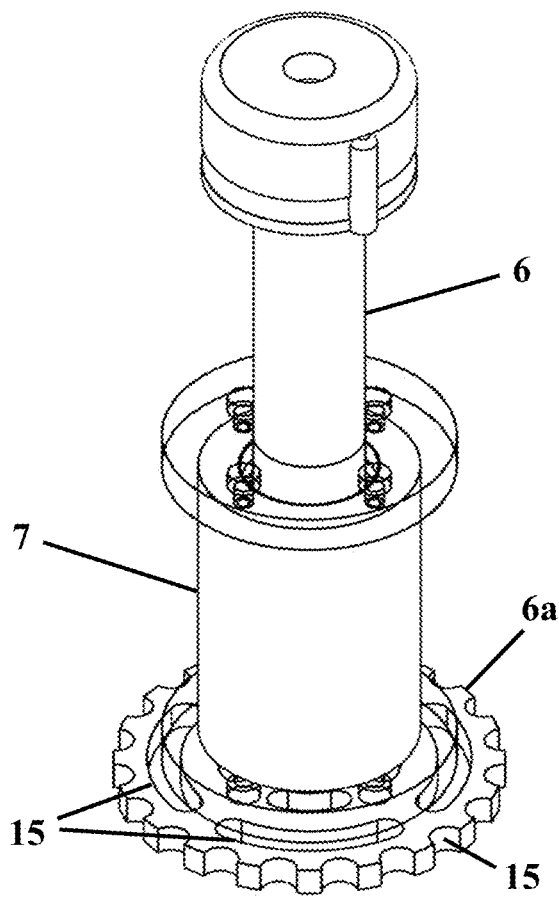
FIG. 10 is a perspective view of the piston and sleeve of the deformable imaging phantom.
Figure 11:
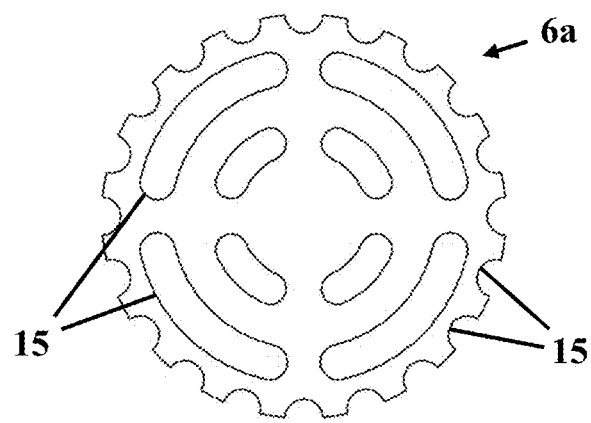
FIG. 11 is a bottom detail view of the piston head of the deformable imaging phantom.

The head 6a of the piston 6 permits the MRI contrast media filling the sealed reservoir 3 to flow past or through the head 6a, such that the MRI contrast media on one side of the head 6a is in fluid communication with the MRI contrast media on the other side of the head 6a. As shown in FIGS. 10 and 11, the head 6a may have a disc-like shape with one or more apertures 16 therethrough, to facilitate the free flow of the MRI contrast media through the head 6a. The apertures 16 may also be located about the periphery of the head 6a to define flow channels between the head 6a and the side wall 2a of the housing 2. Alternatively, the head 6a may have a porous structure. Free fluid flow past or through the head 6a minimizes turbulent flow of the MR contrast media within the sealed reservoir 3, reducing imaging artifacts and allowing the mechanism to move at physiological speeds. In addition, the flow of the MRI contrast media through the apertures 16 in the head 6a and through the open cell foam of the deformable structure 4 produces physiological fluid diffusion within the phantom. This allows for application of certain embodiments of the phantom to diffusion weighted imaging and analysis.

Preferably, the deformable structure 4 is be attached to the piston head 6a by any suitable means of attachment, such as an adhesive, allowing for both motion and deformation of the target 5. A preferred adhesive is an acrylate, which may be applied sparingly to form a strong chemical bond between the deformable structure 4 and the piston head 6a, while minimizing closed cells and resulting air voids, which can introduce MR or CT imaging artifacts. Alternatively, as shown in FIGS. 12 and 13, the deformable structure 4 is attached to the piston 6 and to an end plate 2c mounted within the housing 2 adjacent the end cap 2b. The end plate 2c may be mounted on rails or other guides on the sidewall 2a that allow for free, linear motion of the end plate 2c within the housing 2 or permit the locking of the end plate 2c in place. Locking the end plate 2c permits the deformable structure 4 to be deformed in two ways. Linear motion of the piston 6 compresses or stretches the deformable structure 4 and causes deformation of the shape of the target 5 therein. Alternatively, or in addition to linear motion, a rotational motion of the piston 6 induces a twist of the deformable structure 4 and causes a different deformation of the shape of the target 5 therein.

A motion assembly 9, such as a MR compatible motor system, may be connected to the piston 6 to drive the motion of the piston 6 relative to the housing 2. Preferably, the motion assembly 9 is a MR compatible piezoelectric motor assembly, as described in U.S. Pat. No. 10,090,781 B2 in the name of the present applicant. Alternatively, other types of motion assemblies may be used, such as pneumatic or hydraulic drives. The motion assembly 9 is connected to the piston 6 by way of a shaft 10 that is operatively engaged with the motion assembly 9. The shaft 10 is driven by the motion assembly 9 to provide linear and/or rotational motion to the piston 6. The phantom 1 thereby provides deformable 4D motion with hysteresis for use in 4D motion tracking. Optionally, the motion assembly 9 may be controlled by a programmable controller, capable of generating periodic or aperiodic motion profiles.

Figure 14:
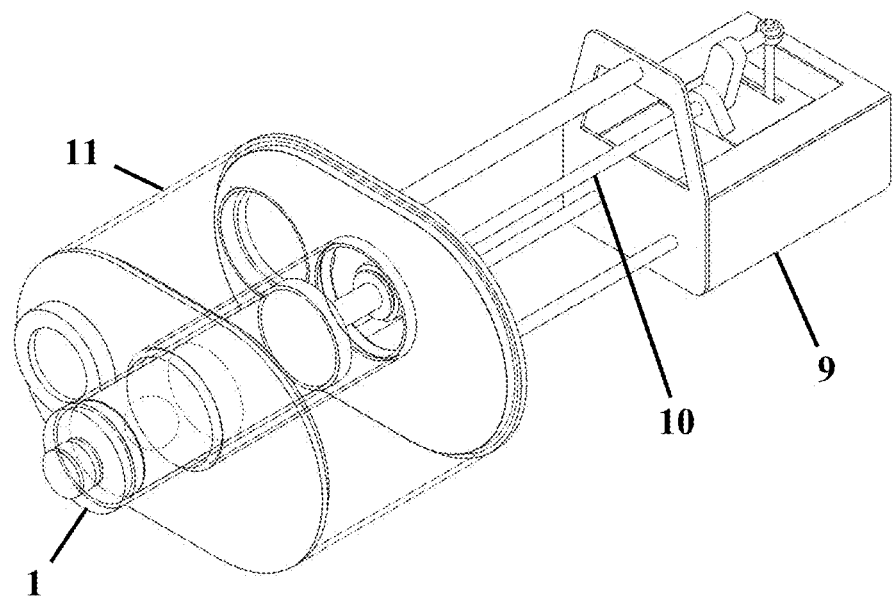
FIG. 14 is a perspective view of the deformable imaging phantom, shown in use with a human thorax phantom and motion assembly.

As shown in FIG. 14, the phantom 1 may be configured for use as an insert in a thorax phantom 11. Preferably, the mounting interface with the thorax phantom 11 includes a locking mechanism to prevent relative motion between the housing 2 and the thorax phantom 11. In particular, locking the housing 2 in place relative to the thorax phantom 11 facilitates use of the phantom 1 in a twist mode. However, the phantom 1 may be configured for use independently or with other types of phantoms or QA devices and may have other geometries, such as an anatomic shape of an organ or tumor.

Optionally, as shown in FIG. 8, the target 5 may have three orthogonal channels 13 therethrough. The channels 13 act as MRI contrast media filled voids forming a jack structure for landmarking the target 5 and improving its flexibility. Various sizes and other geometries of channels 13 or other heterogenous structures may be used in addition to or instead of three orthogonal channels 13, as required by the desired application.

Fiducial markers, or fiducials 14, may be positioned at any desired location within the phantom 1 for modeling verification, such as attached to the target 5 within the deformable structure 4, as shown in FIGS. 6 and 7. The fiducials 14 may be additive or subtractive, positive or negative signal. Preferably, spherical fiducials 14 at least 3 mm in diameter are fixed to the target 5 and positioned on three orthogonal axes. The fiducials 14 provide verification for interpreting the motion of the target on kV or MV CT imaging, for example, in applications such as an EPID panel. Where the fiducials are intended to be used in MV CT applications, they must be of a sufficiently high-density material for visibility, such as an alumina or zirconia ceramic material. Alternatively, the fiducials 14 may be made of another high-density non-metallic material that is visible on MV. In a further alternative, fiducials 14 may not be necessary where the target 5, itself, has a density such that it is visible on kV and MV imaging. Fiducials are also unnecessary for MR only applications.

The deformable structure 4 may be made with a consistent density across the entire deformable structure 4, or, alternatively may have a density gradient. For example, the density of the foam material may be the highest adjacent the end cap 2b and become progressively lower towards the piston 6.

In certain preferred embodiments, the amplitude (range) of motion that the phantom 1 is able to achieve is about 4 cm (+/−20 mm) which is physiologically relevant to the motion of a human diaphragm within the thorax of a patient. Within the thorax the most common organ to gait during treatment is the lungs, which exhibits 2-3 cm of deformation during breathing. From the organ deformation, the tumor itself will move approximately 1 to 1.2 cm each cycle. Finally, the deformation of the organ causes deformation of the tumor which can be quantified in the range of 0-5 mm.

In embodiments that include an end plate 2c, the provides the ability to decouple deformation and motion by allowing the deformable structure 4 and the target 5 to move a certain distance, before the sliding motion of the end plate 2c is stopped. Preferably, the end plate 2c is permitted to move about 2.5 cm before coming into contact with the end cap 2b. Once contact is established the target 5 will begin to exhibit a combination of motion and deformation over the remaining stroke of the amplitude of the system, which is preferably about 1.5 cm. Out of that 1.5 cm, about 0.5 cm of deformation in the linear length of the target 5 is achieved. By limiting the amplitude/stroke of the motor can produce a waveform of +/−2.5 cm that is purely motion, or the motor may be run to produce a waveform in the +/−1.5 cm range to produce a combination of motion and deformation. The customization of the waveform patterns dictates the amount of motion and deformation that is observed.

The present invention has been described and illustrated with reference to an exemplary embodiment, however, it will be understood by those skilled in the art that various changes may be made and equivalents may be substituted for elements thereof without departing from the scope of the invention as set out in the following claims. Therefore, it is intended that the invention not be limited to the particular embodiments disclosed herein.

What is claimed is:

1. A deformable phantom, comprising:
a housing made of a MRI invisible material enclosing and defining a first boundary of a sealed reservoir filled with a MRI signal producing material;
a sleeve reciprocatingly mounted to the housing, extending into the housing, and defining a second boundary of the sealed reservoir;
a piston reciprocatingly mounted within the sleeve, extending into the housing, and defining a third boundary of the sealed reservoir; and
a deformable structure within the boundaries of the sealed reservoir.

2. The deformable phantom of claim 1, wherein the piston and sleeve are configured to move in opposite directions as they move in and out of the housing.

3. The deformable phantom of claim 2, wherein the deformable structure comprises a deformable target within the deformable structure, having a different proton or electron density from the deformable structure.

4. The deformable phantom of claim 3, wherein the deformable structure is an open cell foam structure with the MRI signal producing material filling the interstitial spaces in the foam structure.

5. The deformable phantom of claim 3, wherein the deformable target is ellipsoidal in shape and positioned off-centre within the deformable structure.

6. The deformable phantom of claim 5, wherein the deformable target has three cylindrical channels therethrough, positioned on three orthogonal axes.

7. The deformable phantom of claim 6, wherein one or more high-density fiducial markers are fixed to the deformable target.

8. The deformable phantom of claim 3, wherein the housing has a cylindrical shape with a continuous sidewall and opposing first and second end caps.

9. The deformable phantom of claim 8, wherein the first end cap has an annular shape, defining an aperture, and wherein the piston and sleeve are reciprocatingly mounted concentrically within the first end cap and extend into the housing through the aperture in the first end cap.

10. The deformable phantom of claim 8, wherein the deformable structure is shaped to provide flow channels between the deformable structure and the side wall of the housing.

11. The deformable phantom of claim 3, wherein the piston has a piston head located within the housing, having one or more apertures therethrough.

12. The deformable phantom of claim 11, wherein the deformable structure is attached to the piston head.

13. The deformable phantom of claim 3, wherein the piston is connected to a motion assembly to drive the motion of the piston relative to the housing.

14. The deformable phantom of claim 13, wherein the motion assembly is configured to provide one or both of linear and rotational motion to the piston.

15. The deformable phantom of claim 3, wherein the deformable phantom is configured for use as an insert in a second phantom.

16. The deformable phantom of claim 3, wherein the housing, the MRI signal producing material, the deformable structure, and the deformable target are made of one or more materials having a close susceptibility match to human tissue.

17. The deformable phantom of claim 3, wherein the deformable structure comprises a plurality of deformable targets within the deformable structure, having a different proton or electron density from the surrounding deformable structure.

18. The deformable phantom of claim 3, wherein the deformable structure is enclosed in a coating of deformable material.

19. The deformable phantom of claim 3, wherein the deformable structure is attached at one end to the piston and at an opposing end to an end plate reciprocatingly mounted within the housing.

20. The deformable phantom of claim 3, wherein one or both of the deformable structure and the deformable target are deformable dosimeters.

21. The deformable phantom of claim 20, wherein the deformable dosimeters comprise one or more radiation indicators, selected from the group consisting of: acrylamide and bis-acrylamide monomers, which are susceptible to radiation-induced polymerization; radiochromic dyes; and silicone or urethane rubbers doped with additives, which are susceptible to radiation-induced cross-linking.

22. A deformable phantom, comprising:
a housing made of a MRI invisible material enclosing and defining a first boundary of a sealed reservoir filled with a MRI signal producing material, wherein the sealed reservoir has a first volume portion and a second variable volume portion in fluid communication therewith;
a piston reciprocatingly mounted to the housing, extending into the housing, and defining a second boundary of the sealed reservoir; and
a deformable structure within the boundaries of the sealed reservoir and not exposed to an exterior of the sealed reservoir;
wherein the second variable volume portion varies to accommodate displacement of the fluid MRI signal producing material caused by the movement of the piston.

23. The deformable phantom of claim 22, wherein the deformable structure comprises a deformable target within the deformable structure, having a different proton or electron density from the deformable structure.

24. The deformable phantom of claim 23, wherein the deformable structure is an open cell foam structure with the MRI signal producing material filling the interstitial spaces in the foam structure.

25. The deformable phantom of claim 23, wherein the deformable target is ellipsoidal in shape and positioned off-centre within the deformable structure.

26. The deformable phantom of claim 25, wherein one or more high-density fiducial markers are fixed to the deformable target.

27. The deformable phantom of claim 23, wherein the deformable structure is shaped to provide flow channels between the deformable structure and the side wall of the housing.

28. The deformable phantom of claim 23, wherein the piston has a piston head located within the housing, having one or more apertures therethrough.

29. The deformable phantom of claim 28, wherein the deformable structure is attached to the piston head.

30. The deformable phantom of claim 23, wherein the piston is connected to a motion assembly to drive the motion of the piston relative to the housing.

31. The deformable phantom of claim 30, wherein the motion assembly is configured to provide one or both of linear and rotational motion to the piston.

32. The deformable phantom of claim 23, wherein the deformable phantom is configured for use as an insert in a second phantom.

33. The deformable phantom of claim 23, wherein the housing, the MRI signal producing material, the deformable structure, and the deformable target are made of one or more materials having a close susceptibility match to human tissue.

34. The deformable phantom of claim 23, wherein the deformable structure comprises a plurality of deformable targets within the deformable structure, having a different proton or electron density from the surrounding deformable structure.

35. The deformable phantom of claim 23, wherein the deformable structure is enclosed in a coating of deformable material.

36. The deformable phantom of claim 23, wherein the deformable structure is attached at one end to the piston and at an opposing end to an end plate reciprocatingly mounted within the housing.

37. The deformable phantom of claim 23, wherein one or both of the deformable structure and the deformable target are deformable dosimeters.

38. The deformable phantom of claim 37, wherein the deformable dosimeters comprise one or more radiation indicators, selected from the group consisting of: acrylamide and bis-acrylamide monomers, which are susceptible to radiation-induced polymerization; radiochromic dyes; and silicone or urethane rubbers doped with additives, which are susceptible to radiation-induced cross-linking.

* * * * *